United States Patent [19]

Sussman et al.

[11] Patent Number: 5,266,476
[45] Date of Patent: Nov. 30, 1993

[54] FIBROUS MATRIX FOR IN VITRO CELL CULTIVATION

[75] Inventors: Martin Sussman, Lexington, Mass.; Zvi Bohak, Rehovot; Avinoam Kadouri, Petach Tikva, both of Israel

[73] Assignee: Yeda Research & Development Co., Ltd., Rehovot, Israel

[21] Appl. No.: 869,078

[22] Filed: Apr. 14, 1992

Related U.S. Application Data

[63] Continuation of Ser. No. 709,789, Jun. 3, 1991, abandoned, which is a continuation of Ser. No. 875,691, Jun. 18, 1986, abandoned.

[30] Foreign Application Priority Data

Jun. 18, 1985 [IL] Israel ........................................ 75554

[51] Int. Cl.$^5$ ........................... C12N 5/00; C12N 5/06; C12N 11/08; C12N 11/12
[52] U.S. Cl. ........................... 435/240.23; 435/240.24; 435/240.243; 435/240.25; 435/179; 435/180
[58] Field of Search ...................... 435/240.23, 240.24, 435/240.242, 240.243, 240.25, 285, 286, 179, 180; 210/491, 503, 505, 507, 508

[56] References Cited

U.S. PATENT DOCUMENTS

| | | | |
|---|---|---|---|
| 3,941,661 | 3/1976 | Noteboom | 435/285 |
| 4,144,126 | 3/1979 | Burbidge | 435/240.24 |
| 4,546,083 | 10/1985 | Meyers | 435/285 |
| 4,789,634 | 12/1988 | Müller-Lierheim | 435/285 |
| 4,861,714 | 8/1989 | Dean, Jr. et al. | 435/240.23 |

FOREIGN PATENT DOCUMENTS

1147679 6/1983 Canada ........................ 435/240.23

OTHER PUBLICATIONS

Kruse, Jr. et al. (Eds.) Tissue Culture, 1973 Academic Press, New York, pp. 333-336, 338, 339, 377-379.
Freshney *Culture of Animal Cells.* 1983 Liss, Inc. N.Y. pp. 55-60.

Primary Examiner—George C. Elliott
Attorney, Agent, or Firm—Browdy and Neimark

[57] ABSTRACT

There is provided a matrix and cultivation system for anchorage dependent cells. The matrix is characterized by a substantially increased available effective surface area for cell attachment which is attained by resorting to the use of a fiber network or open-pore foams with suitable pore size. Attachment of the cells can be enhanced by modifying the surface of the substrate. One embodiment comprises a matrix in particle or flake form.

24 Claims, 8 Drawing Sheets

FIBROUS MATRIX FOR IN VITRO CELL CULTIVATION

This application is a continuation of application Ser. No. 07/709,789, filed Jun. 3, 1991, abandoned, which is a continuation of application Ser. No. 06/875,691, filed Jun. 18, 1986, abandoned.

FIELD OF THE INVENTION

The present invention relates to the in vitro cultivation and growth of various living cells, and in particular to methods and devices for in vitro growth of mammalian tissue cells that require (in addition to sterile liquid nutrient media) attachment to a solid surface in order to effectively grow, metabolize nutrients, reproduce, and produce biologically active materials. Such tissue cells are called "anchorage dependent" cells. The provision of suitable surfaces to which such cells will attach themselves, is an essential requisite for their in vitro cultivation.

BACKGROUND OF THE INVENTION

Tissue cell culture is therefore carried out on solid continuous surfaces. On laboratory scale these are in the form of petri-dishes, flat sided bottle or roller bottles. Recent improvements, applicable also to large scale culture have been the development of spheres of various sizes such as microbeads, as well as of ceramic blocks traversed by small rectangular channels. In all these devices the cells adhere and propagate on the available surface of a solid. Cells will attach only to surfaces that have suitable surface compositions and an electrical surface charge. Materials that have proved successful for this purpose are glass, ceramics, polyvinyl chloride, polystyrene, dextran, collagen, and certain other materials. Frequently the cell attachment surfaces of such materials are treated with 95% sulfuric acid, or preferably with a corona or oxygen plasma discharge to improve cell adherence. Under culturing conditions such as those described in (Kruse & Patterson Tissue Culture—Methods and Applications, Academic Press 1983), cells coming in contact with these surfaces will attach themselves to the surface, and reproduce until they cover the surfaces in a contiguous, confluent monolayer. On reaching confluence cell growth ceases. The phenomenon of cell growth cessation when a contiguous layer of cells is achieved is called "contact inhibition" and is a characteristic of non-cancerous cell growth on two dimensional surfaces.

The growth surfaces used at present for in vitro tissue culture suffer from certain serious shortcomings:

a) They provide limited area per unit volume of nutrient medium supplied, so that the number of cells that can be grown per unit volume of nutrient medium is as much as three orders of magnitude smaller than the volumetric densities of cells in in vitro tissue.

b) They require high concentrations of inoculated cells in order to initiate cell growth. Typically cells are introduced to a fresh culture surface at a concentration and number which is 20-30% of the final number reached at confluence and it is usually impossible to inoculate with less then 10% of the number reached at confluence.

c) Cell growth of non-cancerous cells limited to monolayers;

d) Cells tend to detach from their anchorage surface under conditions that include: monolayer saturation; high or low serum concentration; medium depletion, and particularly, viscous shear caused by stirring or perfusion of the culture medium. Cell growth and biosynthesis stop on cell detachment.

Though non cancerous cells are grown on two dimenisonal surfaces, it has long been known that normal cells will also grow in gels, and specifically those of collagen. One such gel is available commerically (trade name "Gelfoam", Upjohn, Kalmazoo). Gels have however a poor dimensional stablility and, due to their internal structure are unsuitable for growing cells to a reasonable density and especially not for systems with medium perfusion. They have therefore not found use for the large scale culture of cells. Their use is limited to laboratory studies of cell morphology, or studies of the "hystotypic" growth of primary cultures (e.g. Dougles et al., In Vitro, 16, 306–312 (1980)).

Also relevant to this invention is the fact that certain cells and particularly cancerous mammalian cells and altered forms of cells such as hybridomas can be grown freely suspended in culture medium or immobilized in small beads of porous gelled material such as carrageenan, agarose, collagen, gelatin and similar starch or protein or polymer materials. Cells may be mixed into such gels prior to casting the gels into the form of small beads or particles that will be suspended in nutrient medium. (Karkare, S. B., Phillips, P. G., Burke, D. H., and Dean Jr., R. C. "Continuous Production of Monoclonal Antibodies by Immobilized Hybridoma Culture" A.C.S. Annual Meeting Phila. Pa., Aug. 27, 1984, available from Verax Corp. Hanover, N.H.).

Alternatively, cells may be immobilized in microcapsules as described by Lim et al., Microencapsulation of Living Cells and Tissues; J. Pharm. Sci., 70, 4: 351-354, April 1981; Nilsson., Entrapment of Animal Cells for Production of Monoclonal Antibodies and other Biochemicals, Nature 302, 629–630, 1973.

The invention herein described also relates to the cultivation of such non-anchorage dependent cells and other cells whose growth and harvesting may be facilitated by some form of immobilization as described above.

SUMMARY OF THE INVENTION

According to the present invention there are provided:

A matrix for use in cell cultivation in vitro providing a high-surface-area substrate the effective area of which is from 10 to about 100 times the area of same projected onto a plane surface, comprising a physiologically acceptable network of fibers having a porosity, or pore volume as a percentage of total volume, of from 40 to about 95% and a pore size of the order of 10 $\mu$m to 100 $\mu$m or an open-pore foamed structure with a pore size of from about 10 $\mu$m 100 $\mu$m the overall height of the matrix being of the order of from 50 $\mu$m to about 500 $\mu$m;

A matrix where the 3-dimensional structure is one of a non-woven fabric from round, flat, non-round, or hollow fibers or combination of such fibers of the order of from 0.5 $\mu$m to 50 $\mu$m diameter or width;

A matrix where the structure is composed of ribbon formed fibers of 2 $\mu$m to 20 $\mu$m width which may be crimped, and where the ratio of width to thickness is 2:1 or more;

A matrix for anchorage dependent cell attachment that has a high surface density by which is meant a high specific surface area, or surface area per unit of projected surface or, high surface area per unit volume of surrounding medium;

A surface that increases the density of cells grown per unit volume of medium by at least one order of magnitude greater than that achievable in flat plate cultures;

A high specific surface cell attachment matrix that may be disposed as a flat sheet;

A matrix that may be disposed as a spiral sheet or as corrugated sheets;

A matrix that may be disposed as suspended cell carrier in a stirred culture tank reactor;

A matrix that can be easily sampled for determining cell numbers;

A matrix that can be easily sampled for microscopic examination;

A matrix that protects cells from impact and viscous shear;

A matrix that inhibits detachment of cells from said surface;

A matrix that permits cell growth to be initiated at low inoculation densities, and consequently permits cell densities and number to increase by more than 10 fold, thus reducing the number of cultures that need to be started to achieve high production of cells and cell products;

A matrix that permits cell growth in multiple layers and in a three dimensional matrix;

A matrix that permits cells to grow in three dimensional non-planar forms;

A matrix that allows rapid inward diffusion of materials such as nutrients, hormones, growth factors and serum components and outward diffusion of metabolic wastes and cell products;

A matrix for growing anchorage-dependent or non-anchorage dependent cells, said matrix providing high internal surface area and high internal volume with pores that are 1 to 20 times the volume of individual cells, said pores being within 100 micrometer of the exterior surface of the matrix so as to provide rapid diffusion throughout and into and out of the matrix;

A matrix for entrapping cells that are not anchorage-dependent, that facilitates the harvesting of such cells in suspension culture;

A matrix for protecting and growing non-anchorage dependent cells at high density while exposed to fluid nutrients that are moving at high velocities and that are under high shear;

A matrix for entrapping or anchoring cells that has a near neutral buoyancy so that particles made of this matrix may be suspended in nutrient medium with minimal amounts of stirring;

A matrix for anchoring or entrapping cells that has a variable buoyancy controlled by the pressure imposed on the cell culture vessel, so as to permit moving the matrix up and down through the nutrient liquid by lowering or raising the pressure in the cell culture vessel;

A process for producing tissue plasminogen activator at high concentrations and in large volumes of culture, while conserving serum and preventing dilution of cell products in excess medium, and means for carrying our such process.

These and other objectives will became apparent from the following detailed disclosure.

DETAILED DESCRIPTION OF PREFERRED EMBODIMENTS

Figure 1A:
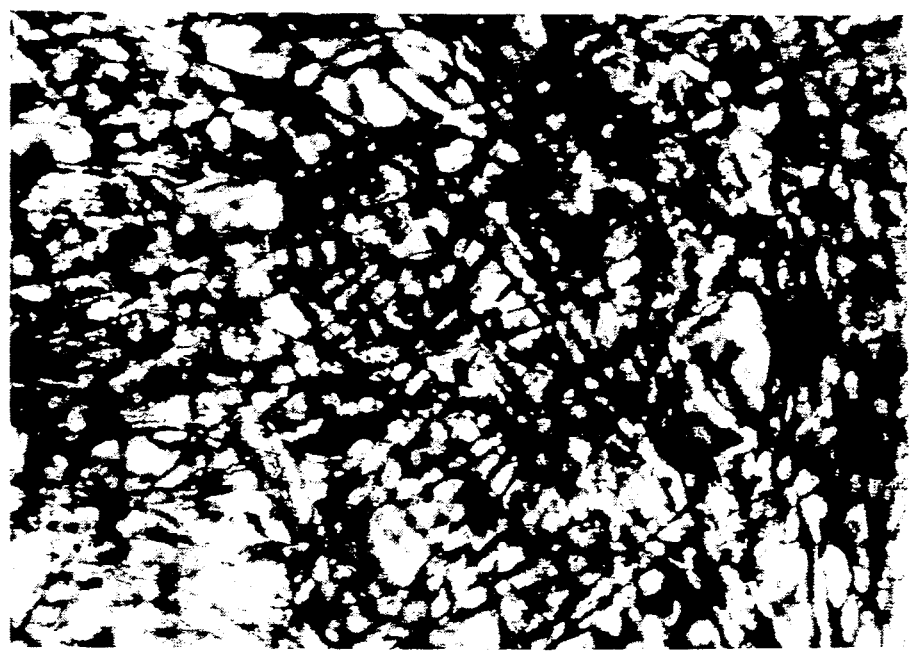
FIGS. 1A and B show fibroblasts grown on polyester sheets. Discs of polyester sheets were cut to fit into 30 mm petri dish. Cells were seeded and allowed to proliferate for (A) 4 days (B) 12 days. The cells were then fixed and stained with gimza stain for microscopic observation.

According to the invention there is provided a growth matrix that substantially increases the available attachment surface for the adherence of the cultivated cells: the increase is by a factor of at least from 10 to 30 times, calculated on the projection of the base on which structures of the invention are supported. Such an increase by a factor of about 10 to 30 times, is per unit layer, and if a plurality of such layers, separated by spacers or the like, is used, the factor of 10 to 30 times applies per each such structure. When the matrix is used in sheet form, preferably non-woven fiber sheets, or sheets of open-pore foamed polymers, the preferred thickness of the sheet is about 50 to 250 $\mu$m, there being provided adequate porosity for cell entrance, entrance of nutrients and for removal of waste products from the sheet, said pores having an effective diameter of 10 $\mu$m to 100 $\mu$m. Such sheets can be be prepared from fibers of various thicknesses, the preferred fiber thickness or fiber diameter range being from about 0.5 $\mu$m to 20 $\mu$m, still more preferred being in the range of 10 $\mu$m to 15 $\mu$m diameter.

A plurality of such sheets can be used, stacked above each other, and in such case suitable spacing means are resorted to. A porous spacer of from 150 μm to about a millimeter generally gives satisfactory results.

The structures of the invention may be supported by, or even better bonded to, a porous support sheet or screen providing for dimensional stability and physical strenght.

Such matrix sheets may also be cut, punched, or shredded to provide particles with projected area of the order of about 0.2 mm$^2$ to about 10 mm$^2$, with the same order of thickness (about 50 to 250 μm), said particles being particulary useful in suspension or fluidized culture.

The present invention relates also to devices or matrices for entrapping and growing non-anchorage dependent cells in open encapsulation, providing a protected micro-environment for growth of cells and facilitating cell harvest.

To produce large quantities of non-anchorage dependent cells, the cells are usually grown in suspension in a nutrient liquid medium that is stirred to ensure that each cell is adequately bathed in nutrients, and that metabolic wastes are carried away from the cell. A certain fraction of the cells is destroyed by impact with the impeller or by high shear. Harvesting cells from conventional suspension culture requires special supplemental equipment such as centrifuges or micro-porous filters. Also cell concentration per cubic centimeter of nutrient liquid is relatively low.

One method of simplifying the harvesting of such cells and increasing their density involves encapsulating the cells in permeable microcapsules as described by the previously cited works of Lim and Nilsson. These microcapsules are larger and denser than the cells they entrap. Consequently they are easily separated from the nutrient medium by settling or by filtration. The microcapsules have certain disadvantages:

they are costly and delicate to produce;

at high density growth, cells at the center of the capsule frequently die;

capsules may burst prematurely losing their content cells;

each new inoculation requires a fresh encapsulation procedure.

The present invention pertains to the provision of forms of materials that provide improved surfaces and morphologies for cell attachment and/or entrapment during in vitro culture, said improved surfaces and morphologies overcoming the shortcomings of currently used attachment surfaces, as well as providing new capabilities for improved culture of other cells not requiring an anchorage surface.

POROUS SHEETS AS CELL GROWTH MATRICES

We have found that certain forms and composition of fibers and certain high porosity membranes provide highly effective supports for culturing cells and particularly anchorage dependent cells; particularly when said fibers are arranged in flat, highly porous, non-woven sheets, or mats, having an appearance like filter or tissue paper, or of thin porous felt. Said non-woven sheets can be made by any of the wide variety of well known techniques for making non-woven fabrics, papers, or felts, which include spin-bonding, thermal bonding, calendering, needling, etc., techniques. The sheets should preferably be free of glue or adhesive coatings not specifically used to promote cell adhesion to the fiber surfaces.

As materials which may be used for the fibers or membranes in accordance with the present invention, any material may be used which is physiologically acceptable, i.e., does not alter the physiological characteristics of the cells, which is stable in the growth medium and to which the cells are capable of attachment, either with or without physical-chemical treatment such as acid wash, corona discharge or poly-D-lysine coating, to promote cell adhesion.

The present invention lies in the particular configuration and confirmation of the material used, and not in the material, per se. Any material or combination of materials having the above properties may be used. As non-limiting examples, there may be mentioned cellulose, cellulose acetate, polyolefins such as polyethylene and polypropylene, polyesters such as polyethyleneterephthalate and mixtures of polyethyleneterephthalate and polyethyleneisophthalate, poly-halogenated-ethylene such as polytetrafluoroethylene and polychloroethylene, polyvinyl chlorides, polystyrenes, polysulfones, fiberglass, ceramics, collagen fibers, natural fibers such as wood pulp, and inert metals such as stainless steel, or combination thereof.

The fibers used to form the non-woven fiber sheets may be in the form of continuous filaments, staple filaments, hollow filaments, pulp, or floc, or combinations of such forms, and are preferably disposed in the sheet in highly disordered, random-like, intertangled, manner; the axes of the fibers forming an open, multi-dimensional array. The porosity of the sheet should range from 40 to 95% with a preferred porosity of 60–80%. Preferred pore-size is between 10 and about 100 μm.

The individual fibers should have deniers (weight in grams of 9000 meters of fiber) of between 0.05 and 5 denier per filament (dpf) with a preferred weight of 1.0 to 1.5 dpf. Fiber cross-section may be round or not, with a preferrred cross-section being that of a ribbon, that may in addition have a crimp imposed along its axis. Fiber width may range from 0.5 to 50 micrometers, but a preferred width is 10 to 15 micrometers. When hollow filaments are incorporated in the non-woven sheet, they may have single or multiple lumens and their denier will generally be greater than solid cross-section fiber, ranging as high as 50 denier per filament.

High porosity membranes suitable for this application must have a sponge-like structure and porosity, and pore dimensions similar to the non-woven fiber mats; that is 40 to 95% porosity and pore size between 10 and 80 micrometers. Pores must be open and have high tortuosity. The polymer matrix should be continuous and can have any composition that promotes cell adhesion. Examples of polymers suitable for porous membrane growth are cellulose, cellulose acetate, polyethylene, polyesters, polyhalogenated ethylenes, polyvinylchlorides, polystyrenes, polysulfones, fiberglass, etc.

Figure 1B:
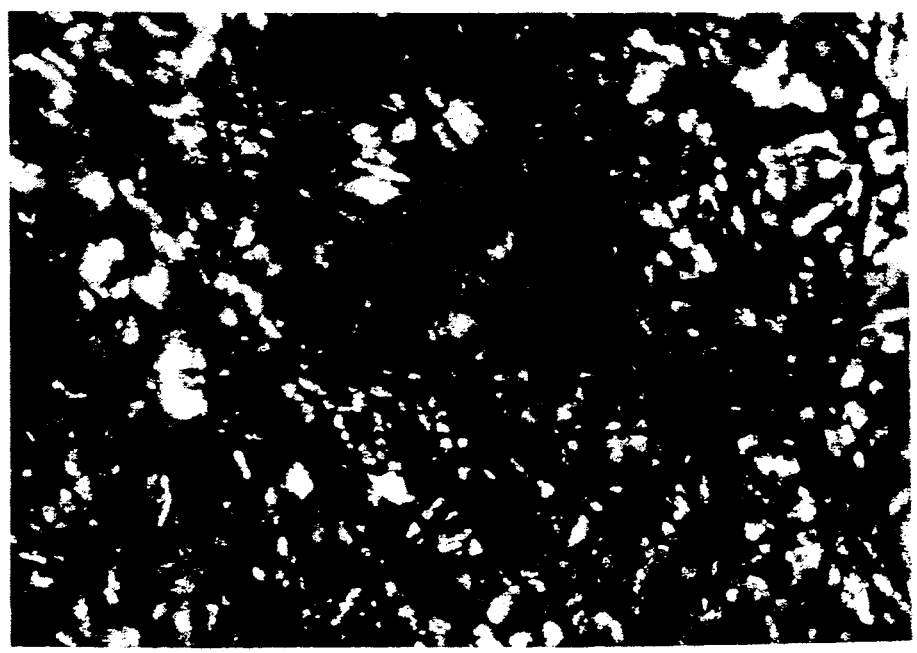

The thickness of the non-woven fiber sheet or porous membrane is an important parameter. Under proper culture conditions many cells inoculated on these sheets grow within the thickness of the sheet, rather than on the top surfaces of the sheet. Cells proliferate among the fibers of the sheet in three dimensions, rather than in two dimensions as in conventional tissue culture bottles, flasks, petri dishes and on microcarrier beads. Cells may attach themselves to more than one fiber (FIGS. 1A and 1B) and cell growth thus takes place in the internal volume of the fiber matrix. The cells form a multilayered tissue-like structure whose thickness is that of the non-woven fiber sheet. To ensure adequate diffusion of nutrient and products to and from the interior of the cell aggregate and to prevent necrosis of cells in the interior of this dense structure, the sheet must be between about 25 and 250 μm thick. A preferred thickness is 100-150 μm. An ideal sheet thickness is approximately equal to the spacing of capillaries that occurs in vivo in the particular kind of tissue being cultured.

Figure 2:
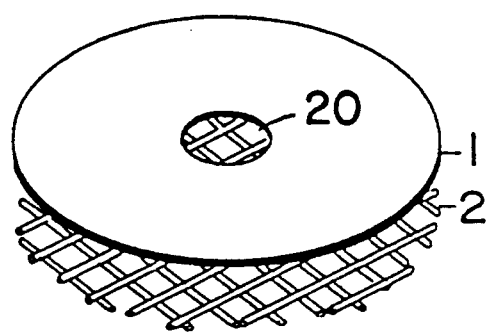
FIG. 2 is a perspective view of a matrix sheet laminated to a polypropylene screen.

The non-woven porous growth matrix sheets may be used alone or they can be thermally bonded to rigid support materials that help the sheets retain their shape, or prevent the sheets from settling into dense contact with each other when used in a close packed array. A particularly useful configuration is to thermally laminate the growth matrix sheet 1 to coarse (1 mm mesh) polypropylene screen 2 (FIG. 2). This also allows adjustment of the net density of the matrix so that it can be neutrally buoyant when used in a suspension culture.

The growth matrix sheets and the support and separator sheets may be provided with means to distribute liquid medium uniformly to all parts of a stack of such sheets and with means to promote the flow of medium parallel to the plane of each matrix sheet. Such means may be integral baffles or channelling orifices as shown by 20 and 21, in FIG. 4a.

Figure 3:
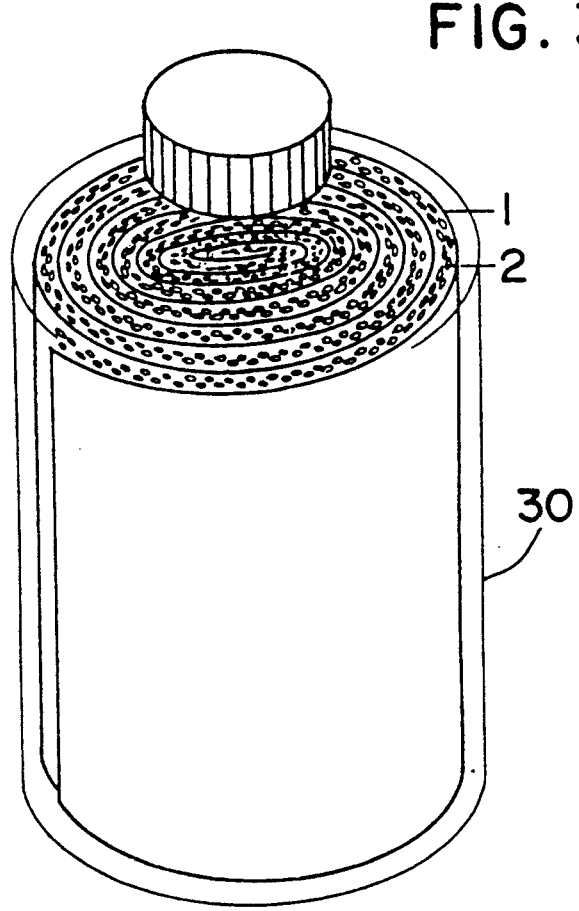
FIG. 3 is a perspective view of spiral sheets of matrix inside a roller bottle.

Growth matrix sheets can be used in many ways. For example, they may be used directly as liners on bottoms of petri dishes or on the inside surfaces of roller bottles, increasing growth surface area by more than one order of magnitude. They can also be used as a spiral sheet of matrix 1 and screen 2 inside a roller bottle 30 (FIG. 3).

Figure 6:
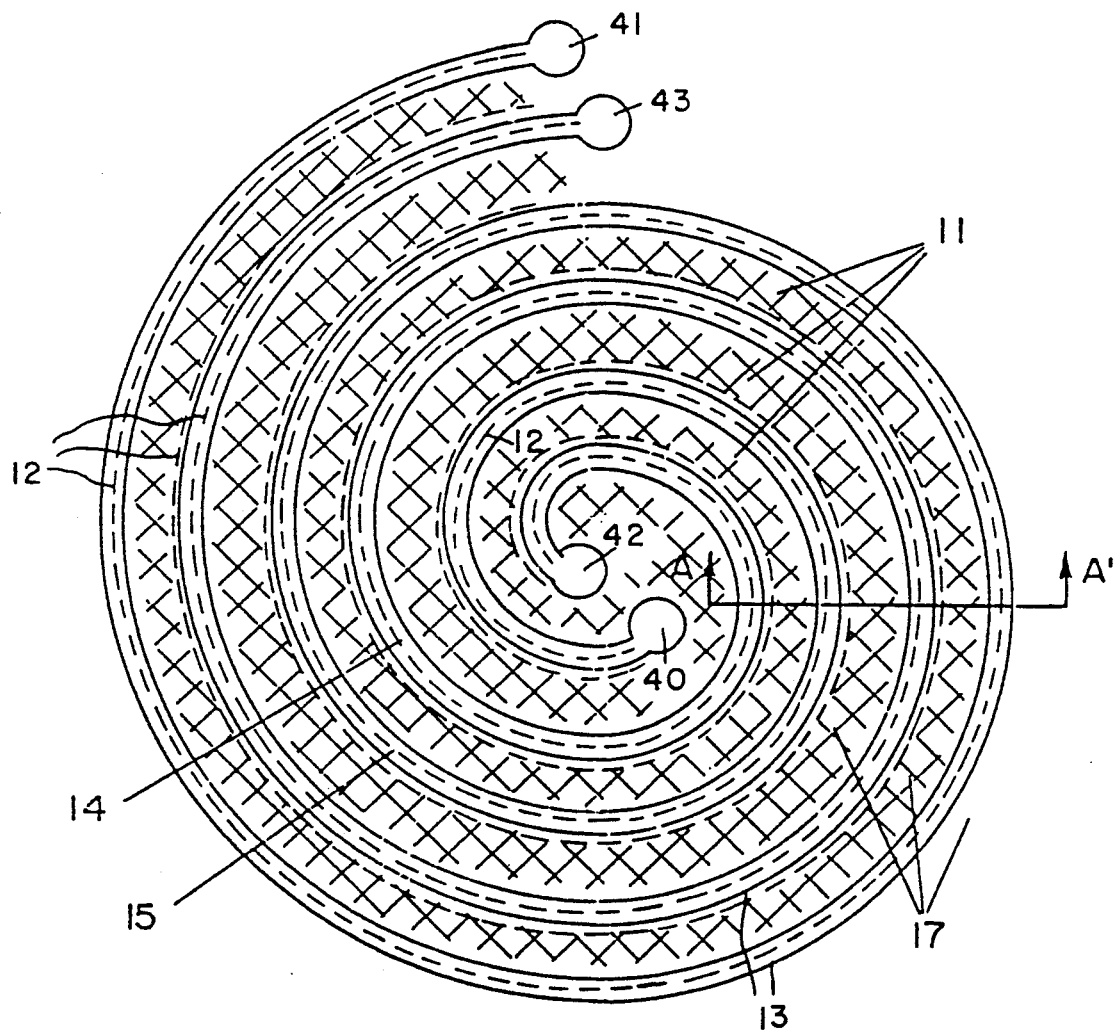
FIG. 6 is a plan view of a spiral assembly of growth matrix and flattened permeable tubes carrying nutrient medium and air. Cell growth occurs in the matrix laminated outside the flattened tubes.
Figure 7:
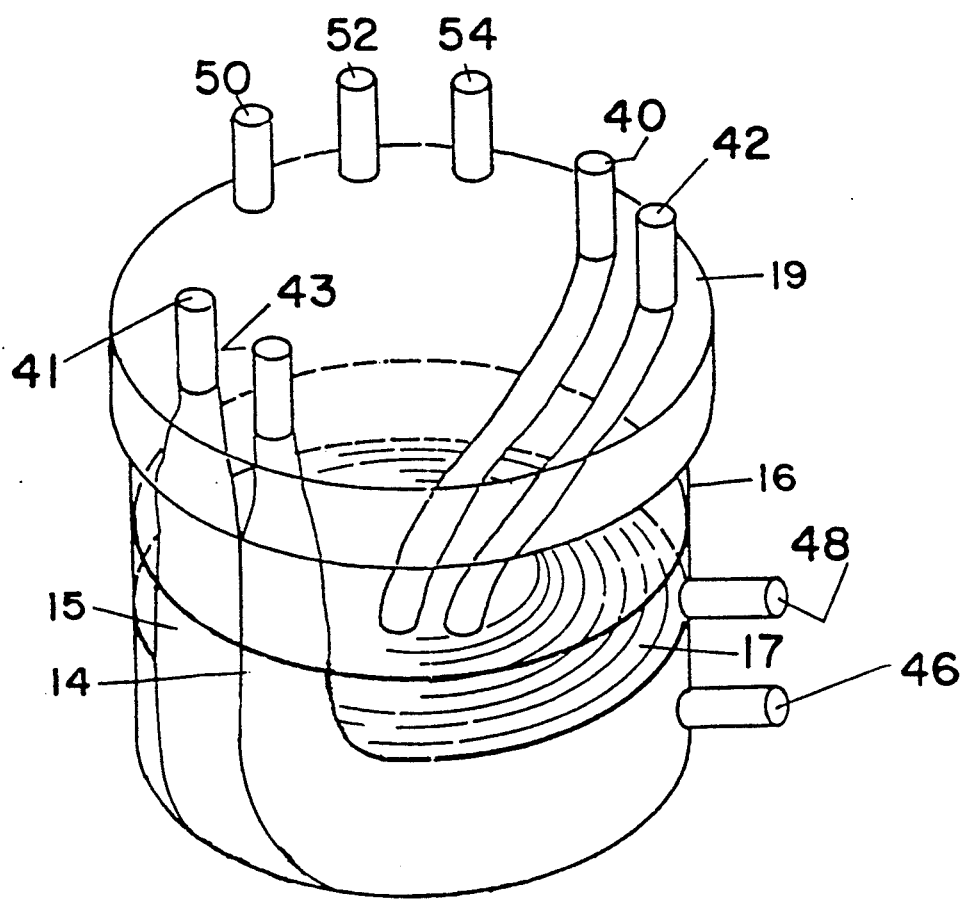
FIG. 7 is a perspective view of a laminated spiral assembly as in FIG. 6, shown in a sterile container containing immersion growth medium, said container having suitable connection for perfusing all fluid channels.
Figure 7A:
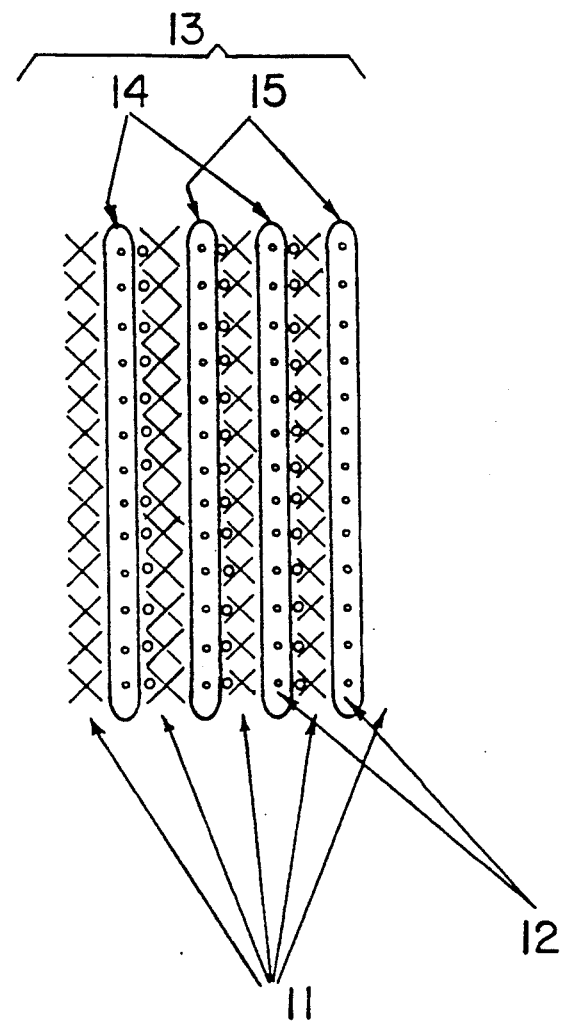
FIG. 7a is a cross-sectional view of a laminated spiral assembly along line A—A' of FIG. 6.
Figure 8:
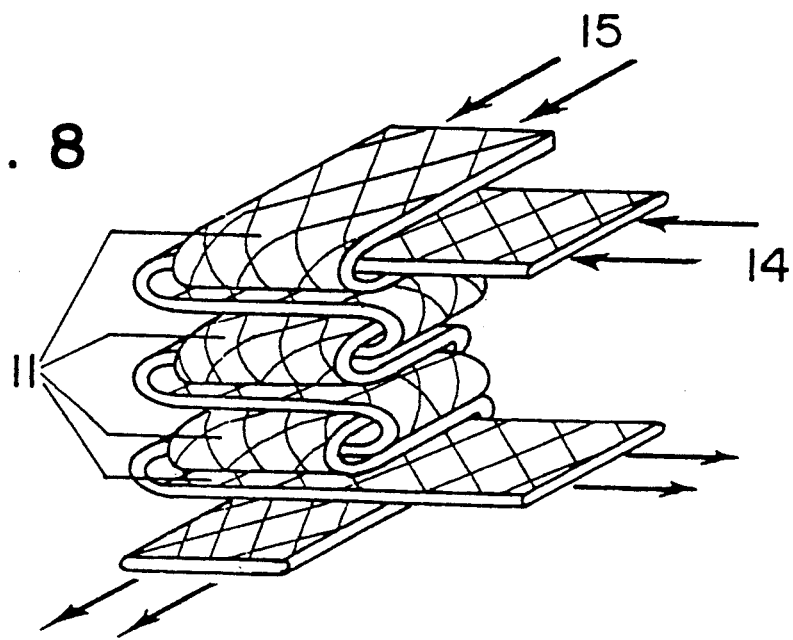
FIG. 8 is a schematic illustration of a laminated stack of growth matrix sheets interleaved with flattened medium and gas tubes, and separator screens.

In FIGS. 6 and 7, matrix sheets 11 are laminated or layered external to and between flattened tubes 13 of permeable or microporous polymers wherein each alternate flattened tube serves as a conduit, the one for liquid nutrient medium 14, the other for gases 15 such as oxygen, air, $CO_2$ and water vapor, the entire assembly being wound into a spiral as shown in FIG. 6, or placed in a laminated interleaved stack (FIG. 8) and immersed in a closed sterile container 16 FIG. 7, filled with nutrient medium 17 and inoculated with cells for cultivation. Gases and nutrient medium are pumped through the flattened permeable tubes 14, 15 in a pulsatile fashion so that cells growing on the porous or non-woven fiber matrix sheet 11 are bathed in gently surging fluid that is never depleted of oxygen or nutrients and in which wastes do not accumulate through stagnation. Four connections 40, 41, 42 and 43 (FIG. 7) generally running through the cover 19 of the assembly serve to introduce and remove gases, and nutrient medium to and from the flattened tubes 14, 15. Probes for monitoring culture parameters such as $PO_2$ 52, pH 50 and glucose concentration 54 may be placed in the growth medium 17 external to the flattened spiral tubes and used to control the nutrient 14 flow rate and composition, as well as the gas 15 $CO_2$ and oxygen content. Polypropylene screens or similar spacers 12 are placed inside each flatted tube and between tubes to maintain minimum separation distances between each layer of the spiral or stack. Access to the cell growth matrix 11 and external or immersion growth medium 17 is made through ports 46,48 that may also be used to perfuse or remove the immersion medium, or for product collection, or for change of medium, or to sample cells.

Figure 4B:
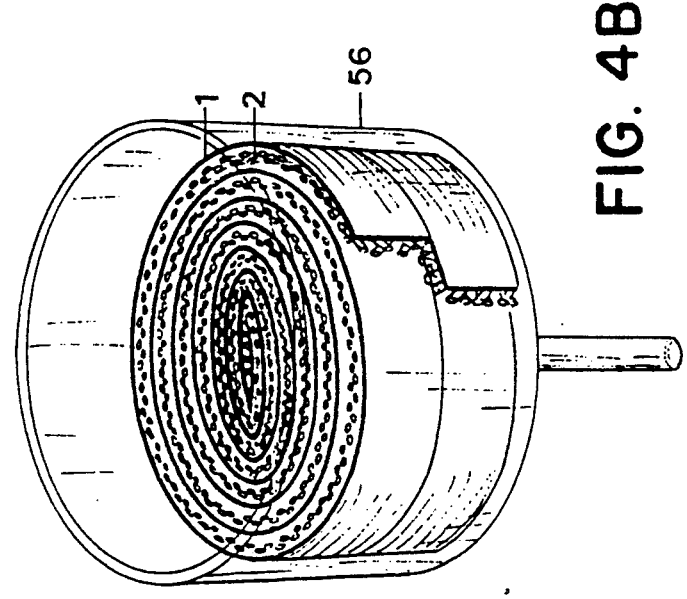
FIG. 4B is a perspective view of matrix sheets spirally wound as packing in a column.
Figure 4A:
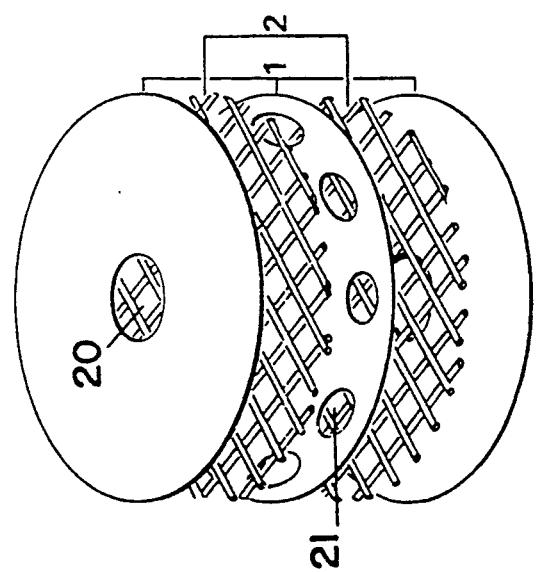
FIG. 4A is an exploded view of circular matrix sheets as packing in a column.

The growth matrix sheets may also be used as packing in a column 56 that is continuously perfused with medium, (FIGS. 4A and 4B). In FIG. 4A the matrix sheets 1 and polypropylene sheets 2 are circular and stacked to form a packing of a column (not shown). Orifices 20 and 21 promote the flow of medium therethrough. FIG. 4B shows a matrix sheet 1 and screen 2 spirally wound and packed in column 56.

The matrices may be used as microcarriers in suspension cultures replacing such materials as modified dextran beads. (Reference "Microcarrier Cell Culture" Pharmacia Chemicals, Uppsala, Sweden (1981)).

When used as microcarriers or as column packing the growth matrix is advantageously laminated to polyproplyene screen (as previously mentioned (FIG. 2)) that are then cut into small discs, squares, rings cruciforms, or corrugated and folded shapes, to give desired hydrodynamic characteristics to the packing or suspension material.

Alternatively, the growth matrix material when used as microcarriers in suspension culture can be cut from fibrous non-woven sheets composed of mixtures of fibers whose density and relative proportions give the sheet a near neutral buoyancy. As an example, circular microdiscs having a diameter of 2 millimeters were stamped from a non-woven sheet composed of a randomly oriented mixture of 20 weight percent polyethylene terephthalate fibers and 80% fibers of polypropylene. Because the polyethylene terephthalate fibers had a specific gravity of 1.33 and the polypropylene fibers a specific gravity of 0.92, the composite non-woven fabric had a density of 1.002, so that microdiscs stamped from this sheet were kept suspended in liquid medium when stirred at much lower speeds then are required to maintain in suspension discs composed of solid polyethylene terephthalate fibers only.

Figure 2A:
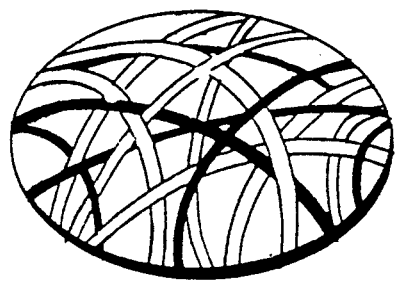
FIG. 2A is a perspective view of a doubly convex suspension culture fibrous microdisc comprised of randomly oriented filaments of a variety of polymers, some of which are capable of thermal bonding, and some of which are hollow and open ended entrapping air or gas bubbles whose size and buoyancy is determined by external pressure in the suspension culture vessel. The thermally bonded edge is formed by stamping through a heated die or punch.
Figure 2B:
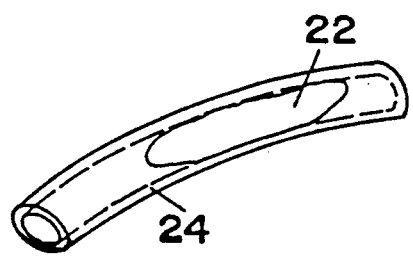
FIG. 2B is a schematic view of a hollow fiber showing gas bubbles trapped in the lumen.

Near neutral buoyancy microdiscs were also made by combining in suitable proportions hollow filament polymer fibers 24 having gas filled lumens, with solid, low denier per filament polymer fibers (FIGS. 2a, 2b). The advantage of microcarriers bearing entrapped gas bubbles 22 is that their buoyancy can be controlled. Because the volume of the entrapped gas increases or decreases as the external pressure on the suspension culture is decreased or increased, the microdiscs are made periodically to float and sink in the nutrient liquid without using an agitator or stirrer. This produces a very gentle washing action and is particularly effective for bringing nutrients to the surface of growing cells and removing metabolic wastes, with cell types that tend to become dislodged from attachment surfaces when stirred. It also eliminates the need for agitators and stirrers, simplifying and reducing the cost of large culture vessels.

A major advantage of this invention is the application of porous matrix cell attachment surfaces to microcarrier tissue cell "suspension culture" (Microcarrier suspension tissue cell culture procedures are described in "Microcarrier Cell Culture," Pharmacia Fine Chemicals, Uppsala, Sweden, (1981); and in the article "Large Scale Production of Tissue Cells" Scientific American Jan (1983)). For suspension culture application the porous sheet is cut into small pieces, each having a projected surface of between about 1 to 100 square millimeters, with a preferred projected area of about one to 20 square millimeters. The shape of said small pieces may take many forms, with a disc or circular form being preferred. The porous matrix cell attachment sheet material may be thermally bonded to materials such as polypropylene screening having a 1 mm or finer mesh, in order to strengthen the porous matrix material and also in order to increase its buoyancy as described previously. It is particularly advantageous to punch such discs using a heated die so that the fibers at the circumferential edge of the disc are thermally bonded or partially fused to each other.

We have discovered on theorectical grounds and verified through experiments that such porous matrix microcarriers require substantially lower concentrations of inoculum (cells introduced at the start of a culture) to initiate successful cell growth. For example in a typical suspension culture of microcarriers (modified dextran beads), the inoculum contains 30% of the number of cells that are harvested at the end of the culture (Fleiscschaker, p. 117, Ph.D. Thesis, June 1982, M.I.T. Dept. of Nutrition and Food Science). We have discovered that when polyester fiber porous matrix microcarriers having a total attachment surface area equal to that of the modified dextran microbeads are used, the inoculum cell content need only be less than about 5% of the final number of cells harvested. This reduction in inoculum size is an immense advantage in large scale production of tissue cells and cell products, in that production from a single culture can be increased by a factor of approximately 6 to 10, and contamination and reseeding problems are diminished.

The effectiveness of fiber or porous matrix microcarriers with low concentrations of cell inocula is not obvious, and is an important discovery. The explanation for this superior effectiveness is as follows:

In a microcarrier suspension culture, for confluent cell growth to occur on an individual microcarrier particle, a minimum number of inoculum cells must collide with and fix themselves to that microcarrier particle. This minimum number of cells will depend to some extent on the cell type, however a typical number is 7 cells per microcarrier particle. (Fleiscschaker, J., pg 171, Ph.D Thesis June 1982, M.I.T. Dept., of Nutrition (Food Sceince). Because the collisions between microcarrier particles and inoculum cells are purely random processes, the fraction of microcarrier particles ($f_i$) experiencing collisions with any number (i) of cells can be estimated by the Poisson Distribution (Equation I):

$$f_i > \lambda^i / (e^\lambda (i)!) \quad (I)$$

where
- i = the number of inoculant cells colliding with a microcarrier particle
- $\lambda$ = average number of inoculum per microcarrier particle, or, inoculum cells per milliliter/microcarrier patricles per milliliter If "n" collisions are required to initiate confluent growth, it follows that the fraction (P), of microcarriers experiencing confluent growth will be one minus the fraction of microcarriers having fewer than n collisions.

$$P = 1 - \sum_{i=0}^{n-1} (f_i) \quad (II)$$

When $n=7$, and $10^5$ cells/ml are inoculated on a normal concentration of $3 \times 10^4$ microcarrier bead particles per milliliter, then $\lambda$, in equation I, is equal to 3.3 cells/microcarrier particle. From equation (I), the fractions of particles experiencing zero to six collisions are found to be:

$f_0=0.04$; $f_1=0.12$; $f_2=0.20$; $f_3=0.22$; $f_4=0.18$; $f_5=0.12$; $f_6=0.07$;

consequently equation (II) be $$P=1-(f_0+f_1+f_2+f_3+f_4+f_5+f_6)=0.05$$

meaning that only one particle in 20 will have 7 or more collisions, and experience confluent cell growth. This culture will therefore fail. Such is in fact the general experience when attempting to inoculate conventional microcarrier cultures at these dilute cell concentrations and conditions (Fleiscschaker ibid. pg. 117).

This statistical reasoning explains the striking superiority of porous or fiber matrix microcarriers. Typically such carriers are 2.0 mm diameter microdiscs stamped from a 150 µm thick non-woven sheet composed of 10 µm diameter polyester fibers. The sheet presents an area for cell attachment of more than 3000 cm²/gram of sheet material. A concentration of 50 such microdiscs per milliliter of culture solution furnishes the same cell attachment area as $3 \times 10^4$ conventional microcarrier beads per milliliter. At $10^5$ cells/ml inoculant concentration the average number of inoculant cells per microdisc, ($\lambda$) is now $10^5/50$, or 2000 cells/per microdisc (in contrast to 3.3 cells per microbead).

The collision frequency of a microdisc with these 2000 cells is magnitudes higher than that of a dextran microcarrier bead with its 3.3 cells. In fact insertion of $\lambda=2000$ in equation (I) shows that disc particles having fewer than even 100 cell collisions are vanishingly rare. Consequently at the same inoculant concentration and surface anchorage area, the probability of a microdisc experiencing more than 100 cell collisions is given by equation II as P is approximately equal to one. Therefore all the microdisc carriers are bombarded with cells and their growth surface reaches saturation on exposure to dilute inocula. Experimentally, 1% inoculation has succeeded in producing confluent growth.

This effect cannot be reproduced with microbeads or non-porous carriers because reducing the number of microbeads reduces the surface available for cell attachment hence microbead suspension culture is limited to a heavy inoculum.

EXAMPLES

1. Material to be used for cell culture matrices were first passed through a discharge from a plasma torch and washed with methanol. The materials were sterilized under a UV light then immersed in a solution of 100 µg/ml poly-D-lysine, and rinsed with sterile water. Cell culture was carried out at 37° C., in an atmosphere of 5% $CO_2$ in air.

2. Unwoven sheets of polyester (0.15 mm nominal thickness, 15 µm fibers) or polypropylene (0.15 mm nominal thickness, 12 µm fibers) were cut into 30 mm diameter circles, and laid on the bottom of 30 mm petri dishes. The same size tissue culture dishes were used as controls. Human dipolid fibroblasts (lung) ($1.5 \times 10^5$ cells) were seeded in each plate with 2.5 ml of DMEM (Dulbeco modified Eagle's medium) +10% serum and the progress of the cultures was examined microscopically. It was observed (FIG. 1A and B) that the cells formed a multi-layered, tissue like structure. The culture was continued until the cells appeared as a congruent mass, whereupon the number of cells in each plate was determined by measuring the amount of DNA. The results (Table 1) show that 7-10 times more cells were obtained in the polymer matrix than on an equal projected area of a regular culture dish.

TABLE 1

| Matrix | No. cells/Cm 2 | Level of confluency as observed by microscope |
| --- | --- | --- |
| Polypropylene | $4 \times 10^5$ | 70% |
| Polyester | $6 \times 10^5$ | 60% |
| Nunc T.C. dish | $4 \times 10^4$ | 100% |

3. Sheets of non-woven fabric were cut into 21×34 cm rectangles, which were attached as 'lines' to the inside of 850 cm² Corning roller bottles. Uncoated roller bottles were used as controls. The fabric lined bottles were each seeded with 1) $0.3 \times 10^7$, 2) $1 \times 10^7$ and 3) $1.5 \times 10^7$ cells. The uncoated bottles were seeded with $1.5 \times 10^7$ cells each. All bottles were then half-filled with medium, and cultures were carried out on a rotating Bellco Roller apparatus 0.5/rev/min. Medium was replaced with fresh medium at 2 day intervals. The uncoated bottle reached confluence, as judged by microscopic examination after 3 days and contained a cell count of $5.7 \times 10^7$ cells. The 'lined' bottles were cultured for an additional 5 days. DNA determinations showed that $3-5 \times 10^8$ cells were obtained in each fabric lined bottle, irrespective of the amount seeded.

4. Sheets 200 cm long and 21 cm wide of non-woven fabric were laminated to a polypropylene screen (1 mm opening, 0.6 mm thick). The laminate was rolled into a spiral and placed within a roller bottle against the inner surface to form a spiral lining 7 layers deep. The roller bottles were seeded each with $1.5 \times 10^7$ cells, and half filled with medium. The progress of culture was followed by removing periodically a piece of the liner, and the growth medium was replaced periodically (based on analysis of glucose and lactic acid) to avoid nutrient exhaustion. The cell proliferated with an average doubling time of 1.2 days and reached after 12 days approximately $4 \times 10^9$ cells per bottle.

Figure 5:
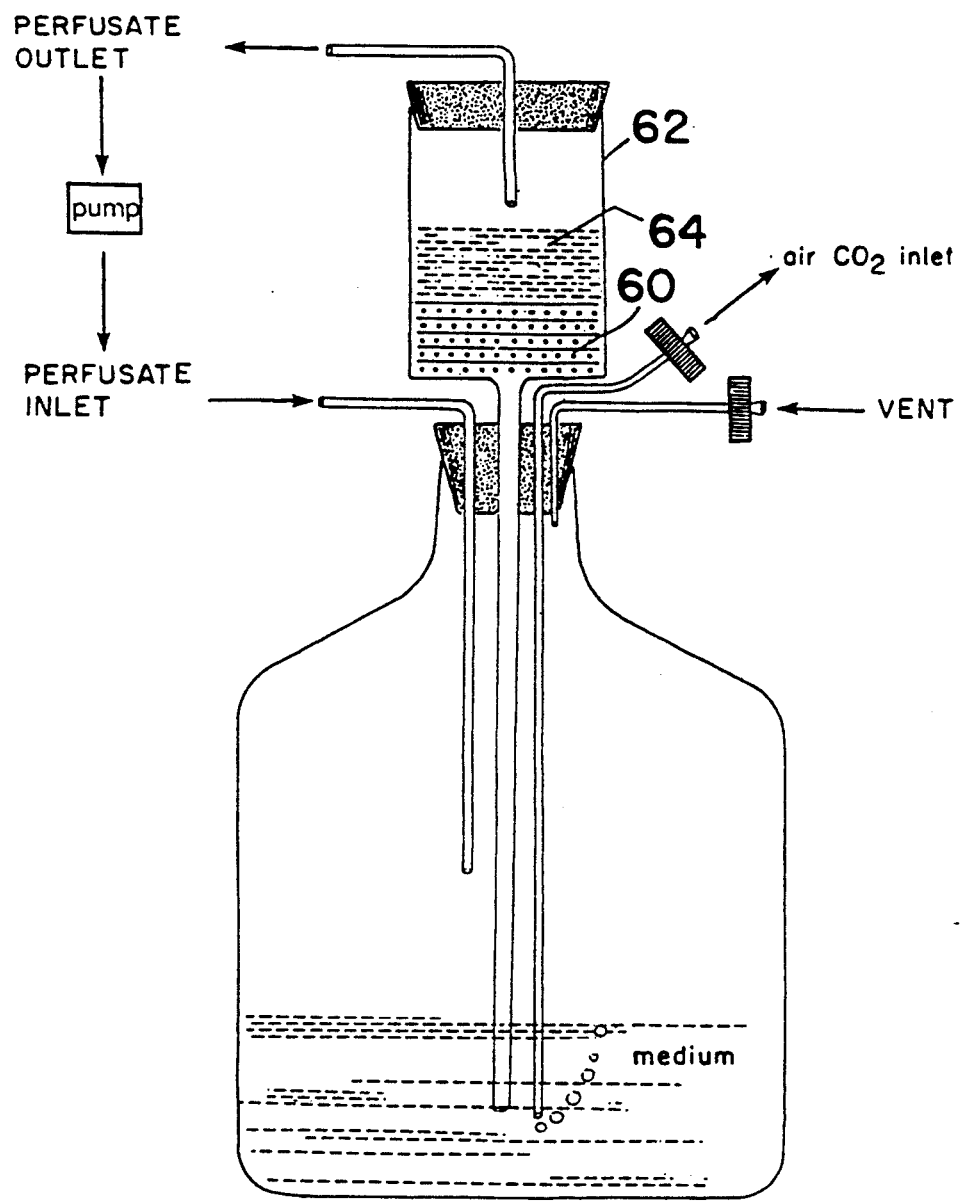
FIG. 5 is an elevational view of a laboratory scale reactor with medium perfusion.

5. Cell culture on non-woven fabrics in a flow - through reactor were tested in a laboratory scale assembly depicted in FIG. 5. Polypropylene or polyester support matrix 60 was introduced into the reactor chamber 62 (FIG. 5) in either of the following forms. i) Stacked circles of a laminate of the unwoven fabric and polypropylene screens. Round holes, 3 mm diameter, were punched (1 or 5 holes per circle) in each circle to control medium flow (FIG. 4A), ii) A rectangle of laminate was rolled into a tight spiral which fitted snugly into the reactor chamber (FIG. 3).

The cells were seeded into the reactor with enough growth medium 64 to cover the matrix. The reactor was closed and the reservoir was filled with medium. After 4 hours of static incubation, medium circulation was started. Pump speed was adjusted to give an initial medium residence time of 25 mins, and as the cells proliferated pumping rate was increased to decrease residence time to about 1 min. The reactor chamber was sampled periodically, by taking out a piece of support, and determining DNA. After 8 days of culture the cell density in the reactor chamber reached $2 \times 10^6$ cells/ml with stacked circles and nearly $7 \times 10^6$ cells/ml with the spiral.

6. Flocks of fibers of rayon (18 μm thick, 0.5-2 mm long), nylon (15 μm 0.5-1.5 mm) and acrylic (10-20 μ×0.2 −1 mm) were treated as in Example 1. One tenth g. of each was layered on the bottom of 50 mm petri dishes, seeded with cells and covered with 3 ml of DMEM+10% serum. The number of cells that attached to the fiber layer was determined after 24 hours. The attachment efficiency was 15-20% on the acrylic fibers, ~35% on the rayon, and nearly 60% on the nylon fibers. A control with a regular tissue culture dish gave 70% attachment efficiency. Nevertheless, all of the floc containing petri dishes contained more cells than the control dish after 8 days of incubation.

7. Sheets of non-woven fabric (400 cm²) were cut into small squares (approximately 3×3 mm) and loaded into Techne 200 ml culture vessel with 100 ml of medium. Bottles were seeded with $1 \times 10^6$, $5 \times 10^6$ and $1.5 \times 10^7$ cells each. Stirring was 30 rpm, and for the first 4 hours the stirrer was on for 30 min and off for 5 min. After that stirring was continuous. On the third day after seeding 70 ml of medium were replaced with fresh medium and thereafter 35 ml were replaced daily. Cell counts were carried out daily by DNA determination. Cell attachment, determined 24 hours after seeding was on the average 67% (56-81%) independent of seeding density. The runs were continued for 4 days after seeding and cell doubling time was on the average about 32 hours. Final cell counts indicated that the cells in each bottle had increased approximately 10 times, and that the rate of increase was insensitive to low concentration of inoculum.

8. Two millimeter diameter microdiscs were punched from a non-woven fiber sheet composed of 1.5 denier per filament polyester fibers and 15 denier per filament hollow polypropylene fibers, using a heated die that thermally bonded the edges of the discs in the manner shown in FIG. 2a giving the disc a doubly convex or lens-like appearance. The discs were then treated as in Example 1, and placed into Techne 200 ml stirred culture bottles at a concentration of 50 discs per ml in 100 ml of medium. IMR-90 human lung fibroblast cells were inoculated at a concentration of $10^5$ cells/ml. Stirring was intermittent and then continuous as in Example 7. Medium was replaced as in Example 7. After 8 days, cells were counted and were found to have a concentration of $4 \times 10^6$ cells per milliliter, proving that an inoculation of 2.5% of final concentration was feasible.

9. A spiral laminated structure comprised of two flattened, one-inch-wide, cellulose dialysis tubes 13; two strips of surface treated non-woven polyester fabric 11 (10 μm fiber diameter); and four strips of polypropylene spacer screening 12 (0.6 μm diameter monofilament, 1 mm opening) was assembled in the form shown in FIG. 6 where each flattened tube 13 had within itself a strip of spacer screening 12, and was bounded on its external flat surfaces by a strip of non-woven fiber-growth matrix 11 and spacer screen 12. The entire assembly was placed in a sterile container 16 and immersed in growth medium 17 as shown in FIG. 7.

The dialysis tubes were each 50 cm long. Nutritional medium without serum was pumped through one flattened tube at a linear flow rate of about 1 cm per second. A sterile mixture of air and 5% $CO_2$ was pumped through the other flattened permeable spiral tube. By suitable means the discharge flow from the gas tube was restricted at two minute intervals so as to cause the spiral tube carrying the gas to periodically swell and contract so as to cause a gentle, reversible, periodic displacement of the growth medium in which the spiral is immersed.

The laminated spiral assembly of fiber growth matrix, spacers, and tube, was immersed in 100 ml of DMEM growth medium containing 10% serum. Hybridomas were inoculated into the serum containing growth medium at a density of $1.5 \times 10^5$ cells/ml. After nine days the concentration in the immersion medium had grown to above $10^7$ cells/ml. The circulating medium contained no serum. The immersion growth medium contained serum and was perfused at a rate that replaced the serum once every 24 hours. After nine days, when full growth had been attained the immersion growth medium was changed to a production immersion medium that contained no serum. The perfusion rate was continued with removal of monoclonal antibody from the immersion medium. The concentration of monoclonal antibody remained stable for 6 weeks at which time the experiment was stopped, although it could have continued.

The spiral assembly separated the growth medium, nutrient medium and gas channels, allowing each to be perfused separately while mass-transfer diffusive contact was maintained among the channels. Serum was conserved and antibody titer was maintained at an optimal level.

It will be obvious to those skilled in the art that various changes may be made without departing from the scope of the invention and the invention is not to be considered limited to what is shown in the drawings and described in the specification.

We claim:

1. A substrate in the form of a sheet for use in cell cultivation in vitro comprising a nonwoven fibrous matrix bonded to a porous support sheet, said matrix comprising a physiologically acceptable three-dimensional network of fibers in the form of a sheet having a pore volume as a percentage of total volume of from 40 to 95% and a pore size of from 10 microns to 100 microns, the overall height of the matrix being from 50 microns to 500 microns, said substrate having a surface area of from about 1 mm$^2$.

2. A substrate according to claim 1 wherein said matrix is made of fiber selected from the group consisting of flat, non-round, and hollow fibers and mixtures thereof, said fibers being of from 0.5 microns to 50 microns in diameter or width.

3. A substrate according to claim 2 wherein said matrix is composed of ribbon formed fibers having a width of from 2 microns to 20 microns, and wherein the ratio of width to thickness of the fibers is at least 2:1.

4. A substrate according to claim 1 having a pore volume as a percentage of total volume of from 60 to 95%.

5. A substrate according to claim 1 wherein the matrix has a height of 50–250 μm.

6. A substrate according to claim 1 wherein the material of the matrix is selected from the group consisting of polyesters, polyalkylenes, polyfluorochloroethylenes, polyvinyl chloride, polystyrene, polysulfones, cellulose acetate, glass fibers, and inert metal fibers.

7. A substrate according to claim 1 wherein the matrix is in a shape selected from the group consisting of squares, rings, discs, and cruciforms.

8. A substrate according to claim 1 wherein the matrix is in the form of a disc.

9. A substrate according to claim 1 wherein the matrix is coated with poly-D-lysine.

10. A substrate according to claim 1 wherein the matrix is comprised of nonwoven polyester fabric and the support is comprised of a sheet of polypropylene mesh with substantially square mesh opening of about one square millimeter.

11. A system for cell cultivation in vitro comprising a substrate in the form of a sheet comprising a nonwoven fibrous matrix bonded to a porous support sheet, said matrix comprising a physiologically acceptable three-dimensional network of fibers in the form of a sheet having a pore volume as a percentage of total volume of from 40 to 95% and a pore size of from 10 microns to 100 microns, the overall height of the matrix being from 50 microns to 500 microns.

12. The system according to claim 11 wherein the substrate is pleated, folded, or spirally wound.

13. The system for cell cultivation in vitro comprising a nonwoven plurality of substrates, each in the form of a sheet, each substrate comprising a fibrous matrix bonded to a porous support sheet, said matrix comprising a physiologically acceptable threedimensional network of fibers in the form of a sheet having a pore volume as a percentage of total volume of from 40 to 95% and a pore size of from 10 microns to 100 microns, the overall height of the matrix being from 50 microns to 500 microns, wherein said sheets are stacked with spacing means between adjacent matrix sheets.

14. A system according to claim 13 wherein said spacing means are porous and have a height of from 150 microns to 1 mm.

15. A system for cell cultivation in vitro comprising a plurality of substrates each in the form of a sheet, each substrate comprising a nonwoven fibrous matrix bonded to a porous support sheet, said matrix comprising a physiologically acceptable threedimensional network of fibers in the form of a sheet having a pore volume as a percentage of total volume of from 40 to 95% and a pore size of from 10 microns to 100 microns, the overall height of the matrix being from 50 microns to 500 microns, said system comprising layers of said matrix sheets between which flattened permeable or microporous tubular conduits are interleaved, said layers of interleaved structure being arranged in a stack or a spiral.

16. A system according to claim 15 wherein the interleaved flattened tubular conduits are composed of films selected from the group consisting of permeable and microporous films of cellulose, polyester, polysulfone, and polyhalogenated ethylene.

17. A system according to claim 16 wherein means are provided for perfusing a fluid cell growth medium outside the interleaved flattened conduits.

18. The system according to claim 17 wherein means are provided for gentle agitation of a fluid cell growth medium outside the interleaved flattened conduits.

19. A system for cell cultivation in vitro comprising a plurality of substrates each in the form of a sheet, each substrate comprising a nonwoven fibrous matrix bonded to a porous support sheet, said matrix comprising a physiologically acceptable threedimensional network of fibers in the form of a sheet having a pore volume as a percentage of total volume of from 40 to 95% and a pore size of from 10 microns to 100 microns, the overall height of the matrix being from 50 microns to 500 microns, each said matrix being in the form of a rectangle which is attached as a liner inside the surface of a container to be used for cell cultivation.

20. A system for cell cultivation in vitro comprising a culture vessel containing a bed of randomly packed substrates, each substrate comprising a fibrous matrix bonded to a porous support sheet, each said matrix comprising a physiologically acceptable three-dimensional network of fibers in the form of a sheet having a pore volume as a percentage of total volume of from 40 to 95% and a pore size of from 10 microns to 100 microns, the overall height of the matrix being from 50 microns to 500 microns.

21. The system according to claim 20 wherein each substrate has a surface area of from about 1 mm$^2$ to about 700 mm$^2$.

22. A substrate in the form of a sheet for use in cell cultivation in vitro comprising a nonwoven fibrous matrix bonded to a porous support sheet, said matrix comprising a physiologically acceptable three-dimensional network of fibers in the form of a sheet having a pore volume as a percentage of total volume of from 40 to 95% and a pore size of from 10 microns to 100 microns, the overall height of the matrix being from 50 microns to 500 microns, said matrix having a surface area of from about 1 mm$^2$ to about 700 mm$^2$ and a height of from about 50 microns to about 250 microns, and said substrate being in a shape selected from the group consisting of squares, rings, discs, and cruciforms.

23. The substrate according to claim 22 wherein the substrate is in the form of a disc.

24. The substrate according to claim 22 wherein the matrix is coated with poly-D-lysine.

* * * * *

UNITED STATES PATENT AND TRADEMARK OFFICE
CERTIFICATE OF CORRECTION

PATENT NO. : 5,266,476
DATED : November 30, 1993
INVENTOR(S) : Sussman et al

It is certified that error appears in the above-indentified patent and that said Letters Patent is hereby corrected as shown below:

Column 9, line 42, equation (I), replace ">" with --=--.

Column 10, line 1, replace "be" with --becomes:--.

Signed and Sealed this

Tenth Day of January, 1995

Attest:

Attesting Officer

BRUCE LEHMAN

Commissioner of Patents and Trademarks